(12) United States Patent
Park et al.

(10) Patent No.: US 12,251,562 B2
(45) Date of Patent: Mar. 18, 2025

(54) APPARATUS AND METHOD FOR CONTROLLING OUTPUT OF SKIN CARE DEVICE

(71) Applicant: AMOSENSE CO., LTD, Cheonan-si (KR)

(72) Inventors: Jin-Pyo Park, Seoul (KR); Won-San Na, Seoul (KR); Jun Ho Park, Seoul (KR)

(73) Assignee: AMOSENSE CO., LTD, Cheonan-si (KR)

( * ) Notice: Subject to any disclaimer, the term of this patent is extended or adjusted under 35 U.S.C. 154(b) by 106 days.

(21) Appl. No.: 16/963,224

(22) PCT Filed: Jan. 17, 2019

(86) PCT No.: PCT/KR2019/000699
§ 371 (c)(1),
(2) Date: Jul. 18, 2020

(87) PCT Pub. No.: WO2019/143147
PCT Pub. Date: Jul. 25, 2019

(65) Prior Publication Data
US 2021/0046308 A1    Feb. 18, 2021

(30) Foreign Application Priority Data

Jan. 19, 2018 (KR) .................. 10-2018-0007314
Jan. 19, 2018 (KR) .................. 10-2018-0007315

(51) Int. Cl.
*A61N 1/04* (2006.01)
*A61N 1/06* (2006.01)
*A61N 1/32* (2006.01)

(52) U.S. Cl.
CPC ............... *A61N 1/328* (2013.01); *A61N 1/06* (2013.01)

(58) Field of Classification Search
CPC . A61N 1/328; A61N 1/06; A61N 1/04; A61B 5/053
(Continued)

(56) References Cited

U.S. PATENT DOCUMENTS 8,731,657 B1 * 5/2014 Shambayati ........... A61N 1/328
607/3
2009/0281537 A1 * 11/2009 Britva .................... A61B 18/18
606/33
(Continued)

FOREIGN PATENT DOCUMENTS

JP        2003189626 A     7/2003
KR       20-0226574 Y     6/2001
(Continued)

OTHER PUBLICATIONS

English Translation of specification for KR101691059B1 A radio frequency medical device (Year: 2016).*
(Continued)

*Primary Examiner* — Nicole F Lavert
(74) *Attorney, Agent, or Firm* — Maschoff Brennan

(57) ABSTRACT

Disclosed is an apparatus for controlling the output of a skin care device, which can reduce a peak power to be output to the skin, by suppressing a sudden current change when a direct current voltage is converted into an alternating current voltage. The disclosed apparatus for controlling the output of a skin care device: amplifies a direct current voltage and outputs same; converts the output direct current voltage into an alternating current voltage with a set frequency and outputs same to a pair of contact electrodes; and detects the skin current according to changes in the resistance of the skin to which the alternating current voltage is applied, so as to control the amplification of the direct current voltage.

3 Claims, 14 Drawing Sheets

(58) Field of Classification Search
USPC .......................................................... 607/62
See application file for complete search history.

(56) References Cited

U.S. PATENT DOCUMENTS

| | | | | |
|---|---|---|---|---|
| 2014/0249522 | A1* | 9/2014 | Adanny | A61N 1/0476 |
| | | | | 606/34 |
| 2016/0184602 | A1 | 6/2016 | Kim | |
| 2016/0346561 | A1* | 12/2016 | Ron Edoute | A61F 7/00 |
| 2017/0281941 | A1 | 10/2017 | Page et al. | |
| 2017/0333705 | A1* | 11/2017 | Schwarz | A61N 1/328 |
| 2018/0161589 | A1* | 6/2018 | Beyer | A61N 1/32 |
| 2018/0192940 | A1* | 7/2018 | Shimazu | A61B 10/00 |
| 2019/0046794 | A1* | 2/2019 | Goodall | A61N 1/36014 |
| 2020/0390642 | A1* | 12/2020 | Kim | A61H 15/0092 |

FOREIGN PATENT DOCUMENTS

| | | |
|---|---|---|
| KR | 10-2004-0085440 A | 10/2004 |
| KR | 101451961 B1 | 10/2014 |
| KR | 10-2016-0128079 A | 11/2016 |
| KR | 10-2017-0105211 A | 9/2017 |
| WO | 98/26841 A1 | 6/1998 |

OTHER PUBLICATIONS

KR Office Action dated May 18, 2020 as received in Application No. 10-2018-0007314.
KR Office Action dated May 18, 2020 as received in Application No. 10-2018-0007315.
CN Office Action dated Aug. 30, 2024 in application 201980007725.4.

* cited by examiner

FIG. 3

| OUTPUT STAGE | AMPLIFIED MODULE OUTPUT (V) | CONVERTED MODULE OUTPUT (Vp-p) | CURRENT LIMITATION (A) |
|---|---|---|---|
| 1 | 4.4 | 55 | INPUT REFERENCE 1A |
| 2 | 5.1 | 66 | |
| 3 | 5.8 | 75 | |

APPARATUS AND METHOD FOR CONTROLLING OUTPUT OF SKIN CARE DEVICE

TECHNICAL FIELD

The present disclosure relates to a skin care device, and more particularly, to an apparatus and a method for controlling the output of a skin care device which care for a skin by applying a high frequency current to the skin.

BACKGROUND ART

Generally, a skin care device may be classified into a skin care device which transfers ultrasound to a user's skin (hereinafter, an ultrasound type skin care device) and a skin care device which applies a current (hereinafter, a current type skin care device).

The ultrasound type skin care device massages the skin by physical vibrations through ultrasound. The current type skin care device applies a micro-current to the user's skin to remove sebum, waste, or the like or to deeply absorb skin nutrients into the skin.

The current type skin care device applies a high frequency current to the skin. The current which is output from the skin care device is applied to a dermal layer of the skin through a pair of electrodes in contact with the skin. The current type skin care device may rotate water molecules in the dermal layer by applying the current, thereby preventing the dermal layer from collapsing, and improving skin wrinkles of the user.

Since the current type skin care device rotates the water molecules in the dermal layer by applying the current, the temperature of the dermal layer increases due to the rotational energy which is generated when the water molecules rotate. There is a problem in that the user feels hot, or the user's skin is burnt in severe cases due to an increase in the temperature of the dermal layer.

Accordingly, various methods for the current type skin care device have been studied to prevent the occurrence of burns due to the increase in the temperature of the dermal layer caused by applying the current.

As an example, the skin care device is re-driven after a set time elapses after the power is turned off when the skin temperature is a set temperature or more, thereby preventing the occurrence of burns due to the increase in the temperature. However, there is a problem in that the conventional current type skin care device has the decreased skin care efficacy because the change in the skin temperature is severe by turning on or off the power, and it is difficult to accurately measure the temperature of the dermal layer.

As another example, the conventional skin care device prevents burns through a pulse width modulation (PWM) control of a current applied to the skin. However, there are problems in that since the skin care device is disposed close to the human body, electromagnetic waves affect the human body, and it is difficult to maintain the current applied to the skin at the set frequency, thereby degrading the skin care efficacy.

Further, there is a problem in that the conventional current type skin care device outputs a pulse-width modulated alternating current power (alternating current), such that a high power (current) is instantaneously applied to the skin at the peak power. At this time, the user may feel hotness or sting, or get electric shock in severe cases because a high power (current) is instantaneously applied to the skin.

DISCLOSURE

Technical Problem

The present disclosure is intended to solve the above problems, and an object of the present disclosure is to provide an apparatus and a method for controlling the output of a skin care device, which apply to a skin a second alternating current voltage having a peak-to-peak voltage lower than a first alternating current voltage when a skin current generated by applying the first alternating current voltage reaches a set current, thereby minimizing a change in the skin temperature.

Further, another object of the present disclosure is to provide an apparatus for controlling the output of a skin care device, which suppresses a sudden change in a current when a direct current voltage is converted into an alternating current voltage, thereby decreasing a peak power which is output to the skin.

Technical Solution

For achieving the objects, an apparatus for controlling the output of a skin care device according to an exemplary embodiment of the present disclosure includes: an amplification module which amplifies and outputs a direct current voltage, a conversion module which converts the direct current voltage output from the amplification module into an alternating current voltage having a set frequency to output the alternating current voltage to a pair of contact electrodes, a peak decreasing module which decreases a maximum peak current of an alternating current generated upon switching of the alternating current voltage output from the conversion module, a current detection module which detects a skin current according to a change in a resistance of a skin to which the alternating current voltage is applied, and a control module which controls the driving of the amplification module based on the skin current.

For achieving the objects, an apparatus for controlling the output of a skin care device according to another exemplary embodiment of the present disclosure includes: a current detection module which detects a skin current according to a change in a resistance of a skin to which an alternating current voltage is applied and a control module which controls the output of the alternating current voltage of the skin care device based on the skin current, in which the control module controls the skin care device to output a first alternating current voltage when the skin current is smaller than a maximum set current, and to output a second alternating current voltage having a peak-to-peak voltage lower than the first alternating current voltage when the skin current is the maximum set current or more.

For achieving the objects, a method for controlling the output of a skin care device according to an exemplary embodiment of the present disclosure includes: amplifying a direct current voltage, converting the amplified direct current voltage into a first alternating current voltage having a set frequency, outputting the first alternating current voltage through a pair of contact electrodes, detecting a skin current according to a change in a resistance of a skin to which the first alternating current voltage is applied, converting the direct current voltage into a second alternating current voltage having a set frequency when the skin current is a maximum set current or more, and outputting the second alternating current voltage having a peak-to-peak voltage lower than the first alternating current voltage through the pair of contact electrodes.

Advantageous Effects

The apparatus and method for controlling the output of the skin care device may apply the second alternating current voltage having the peak-to-peak voltage lower than the first alternating current voltage to the skin when the skin current generated by applying the first alternating current voltage reaches the set current, thereby minimizing the change in the skin temperature as compared to the conventional skin care device in which the power is turned off when the skin temperature is the set temperature or more.

Further, the apparatus and method for controlling the output of the skin care device may decrease the alternating current voltage applied to the skin when the skin current increases due to the increase in the skin temperature, thereby minimizing the change in the skin temperature to minimize the degradation of the skin care efficacy.

Further, the apparatus and method for controlling the output of the skin care device may vary the peak-to-peak voltage of the alternating current voltage applied to the skin to prevent the burns of the skin, thereby minimizing the influence of the electromagnetic waves as compared to the conventional skin care device which prevents the burns through the pulse width modulation control, and may constantly maintain the frequency of the alternating current voltage applied to the skin, thereby preventing the degradation of the skin care efficacy.

Further, the apparatus for controlling the output of the skin care device may suppress the sudden change in the current when the direct current voltage is converted into the alternating current voltage, thereby decreasing the peak power which is output to the skin.

Further, the apparatus for controlling the output of the skin care device may prevent the maximum peak power from being applied to the skin upon switching of the alternating current power applied to the skin, thereby preventing the user from feeling the hotness, sting, and getting electric shock due to the maximum peak power.

Further, the apparatus for controlling the output of the skin care device decrease the peak power, thereby evenly transmitting the power.

DESCRIPTION OF DRAWINGS

FIG. 3 is a diagram for explaining an amplification module of FIG. 2.

MODE FOR INVENTION

Figure 1:
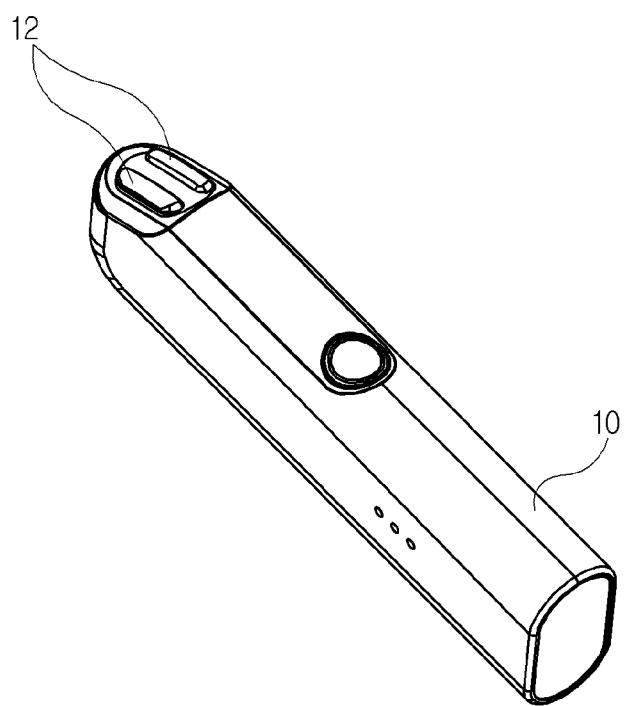
FIG. 1 is a diagram for explaining a skin care device to which an apparatus for controlling the output applied according to an exemplary embodiment of the present disclosure.

Hereinafter, the most preferred embodiments of the present disclosure will be described with reference to the accompanying drawings in order to specifically describe the embodiments so that those skilled in the art to which the present disclosure pertains may easily implement the technical spirit of the present disclosure. First, in adding reference numerals to the components of each drawing, it should be noted that the same components have the same reference numerals as much as possible even if they are displayed in different drawings. Further, in describing the present disclosure, when it is determined that the detailed description of the related well-known configuration or function may obscure the gist of the present disclosure, the detailed description thereof will be omitted.

Referring to FIG. 1, an apparatus for controlling the output according to an exemplary embodiment of the present disclosure is mounted to a main body of a skin care device 10. As an example, the apparatus for controlling the output is formed of a printed circuit board (PCB) and installed inside the main body of the skin care device 10.

The skin care device 10 has a pair of contact electrodes 12 exposed to the outside of the body. The skin care device 10 applies an alternating current having a set frequency (for example, about 1 MHz) to the skin as the pair of contact electrodes 12 contact the skin. Accordingly, the alternating current flows between the pair of contact electrodes 12 and the skin.

The alternating current which is output from the skin care device 10 is applied to a dermal layer. Water molecules exist in the dermal layer, and the water molecules rotate as the alternating current is applied to the dermal layer. The dermal layer increases in temperature due to the rotational energy of the water molecules.

Meanwhile, the skin has a skin resistance, and the skin resistance is different from person to person. There is a characteristic in that the skin resistance decreases as the temperature of the dermal layer increases.

The apparatus for controlling the output according to an exemplary embodiment of the present disclosure measures the skin temperature using the characteristic of skin resistance. That is, the apparatus for controlling the output measures the skin current flowing through the electrode in contact with the skin. At this time, since the skin resistance decreases when the skin temperature increases, an increase in the skin current means an increase in the skin temperature, and a decrease in the skin current means a decrease in the skin temperature.

The apparatus for controlling the output compares the measured skin current with a set current (for example, maximum current or minimum current). The apparatus for controlling the output varies the voltage level of the alternating current voltage output from the skin care device 10 to the skin based on the comparison result. At this time, the apparatus for controlling the output decreases the voltage level of the alternating current voltage when the skin current reaches the maximum current. The apparatus for controlling the output increases the voltage level of the alternating current voltage when the skin current reaches the minimum current.

To this end, the apparatus for controlling the output controls the ON/OFF of an amplifier (for example, boost converter) disposed between a battery 14 and a contact electrode 12 to increase or decrease the voltage level of the alternating current voltage which is output from the skin care device 10. At this time, when the skin current reaches the maximum current, the apparatus for controlling the output turns off the amplifier to decrease the voltage level of the alternating current voltage output from the skin care device 10. The apparatus for controlling the output re-drives the amplifier to increase the voltage level of the alternating current voltage output from the skin care device 10 when a set time elapses after the amplifier is turned off or the skin current reaches the minimum current.

Accordingly, the apparatus for controlling the output constantly maintains the frequency and varies only the voltage level of the alternating current voltage according to the skin temperature (that is, skin current). The apparatus for controlling the output may vary the voltage level of the alternating current voltage to apply the alternating current voltage to the skin, thereby maintaining the alternating current voltage at the set frequency to prevent the skin care efficacy from being degraded while minimizing the difference of the skin temperature.

Meanwhile, the apparatus for controlling the output suppresses the sudden change in the current when the direct current voltage is converted into the alternating current voltage to decrease the peak power which is output to the skin. The apparatus for controlling the output decreases the peak power to apply the alternating current voltage having an output waveform close to a sinusoidal waveform to the skin.

Accordingly, the apparatus for controlling the output may prevent an instantaneous increase in the alternating current power (alternating current) applied to the skin, thereby preventing an increase in the skin temperature, skin sting, and electric shock of the user.

At the same time, the apparatus for controlling the output may decrease the peak power of the alternating current power, thereby evenly applying power to the skin to maximize the skin care efficacy.

Figure 2:
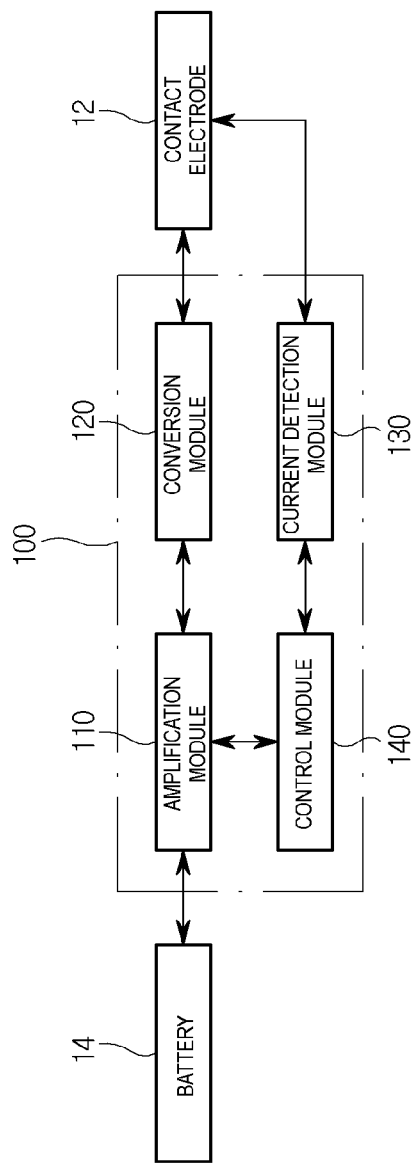
FIG. 2 is a block diagram for explaining an apparatus for controlling the output according to a first exemplary embodiment of the present disclosure.

Referring to FIG. 2, the apparatus for controlling the output 100 according to a first exemplary embodiment of the present disclosure includes an amplification module 110, a conversion module 120, a current detection module 130, and a control module 140. Here, the apparatus for controlling the output 100 has been described as including all of the amplification module 110, the conversion module 120, the current detection module 130, and the control module 140, but is not limited thereto, and the amplification module 110 and the conversion module 120 may also be included in the skin care device 10.

The amplification module 110 amplifies the direct current voltage output from the battery 14 under the control of the control module 140. Here, the direct current voltage amplified by the amplification module 110 means a first direct current voltage described in the claims.

The amplification module 110 amplifies the voltage level of the direct current voltage step by step depending upon output stages (for example, first stage to third stage) which is set in the skin care device 10. The amplification module 110 amplifies the direct current voltage to have a higher voltage level as the output stage is higher. Hereinafter, the direct current voltage amplified by the amplification module 110 is described as an amplified direct current voltage. As an example, the amplification module 110 is a boost converter.

As an example, referring to FIG. 3, when a direct current voltage of about 4.2V is applied from the battery 14, the amplification module 110 outputs an amplified direct current voltage of about 4.4V when the output stage is the first stage, outputs an amplified direct current voltage of about 5.1 V when the output stage is the second stage, and outputs an amplified direct current voltage of about 5.8 V when the output stage is the third stage.

The conversion module 120 converts the amplified direct current voltage into an alternating current voltage. The conversion module 120 converts the amplified direct current voltage amplified by the amplification module 110 into the alternating current voltage having the set frequency. At this time, as an example, the conversion module 120 is a push pull converter. Here, a first alternating current voltage described in the claims means an alternating current voltage obtained by converting the direct current voltage amplified by the amplification module 110, and a second alternating current voltage means an alternating current voltage obtained by converting the direct current voltage not amplified by the amplification module 110.

The conversion module 120 outputs the converted alternating current voltage to the pair of contact electrodes 12. The pair of contact electrodes 12 apply the alternating current voltage to the contacted skin. Accordingly, an alternating current flows between the contact electrode 12 and the skin, and the skin resistance varies.

As an example, referring to FIG. 3, the conversion module 120 outputs an alternating current voltage having a peak-to-peak voltage of about 55 V when the output stage is the first stage, outputs an alternating current voltage having a peak-to-peak voltage of about 66 V when the output stage is the second stage, and outputs an alternating current voltage having a peak-to-peak voltage of about 75V when the output stage is the third stage.

The current detection module 130 detects a skin current according to a change in the skin resistance after the alternating current voltage is applied. The current detection module 130 detects a current value in the pair of contact electrodes 12 as the skin current. The detection module transmits the detected skin current to the control module 140.

The skin current detected by the current detection module 130 is a current value corresponding to the skin resistance. At this time, as the alternating current voltage is applied to the skin, a change in the temperature occurs in a dermal layer of the skin, and the skin resistance varies depending upon the change in the temperature. Accordingly, the skin current detected by the current detection module 130 increases as the skin temperature is higher, and decreases as the skin temperature decreases.

The control module 140 controls the driving of the amplification module 110 based on the skin current detected by the current detection module 130. The control module 140 controls the driving of the amplification module 110 based on the skin current detected by the current detection module 130 and a set current.

Figure 4:
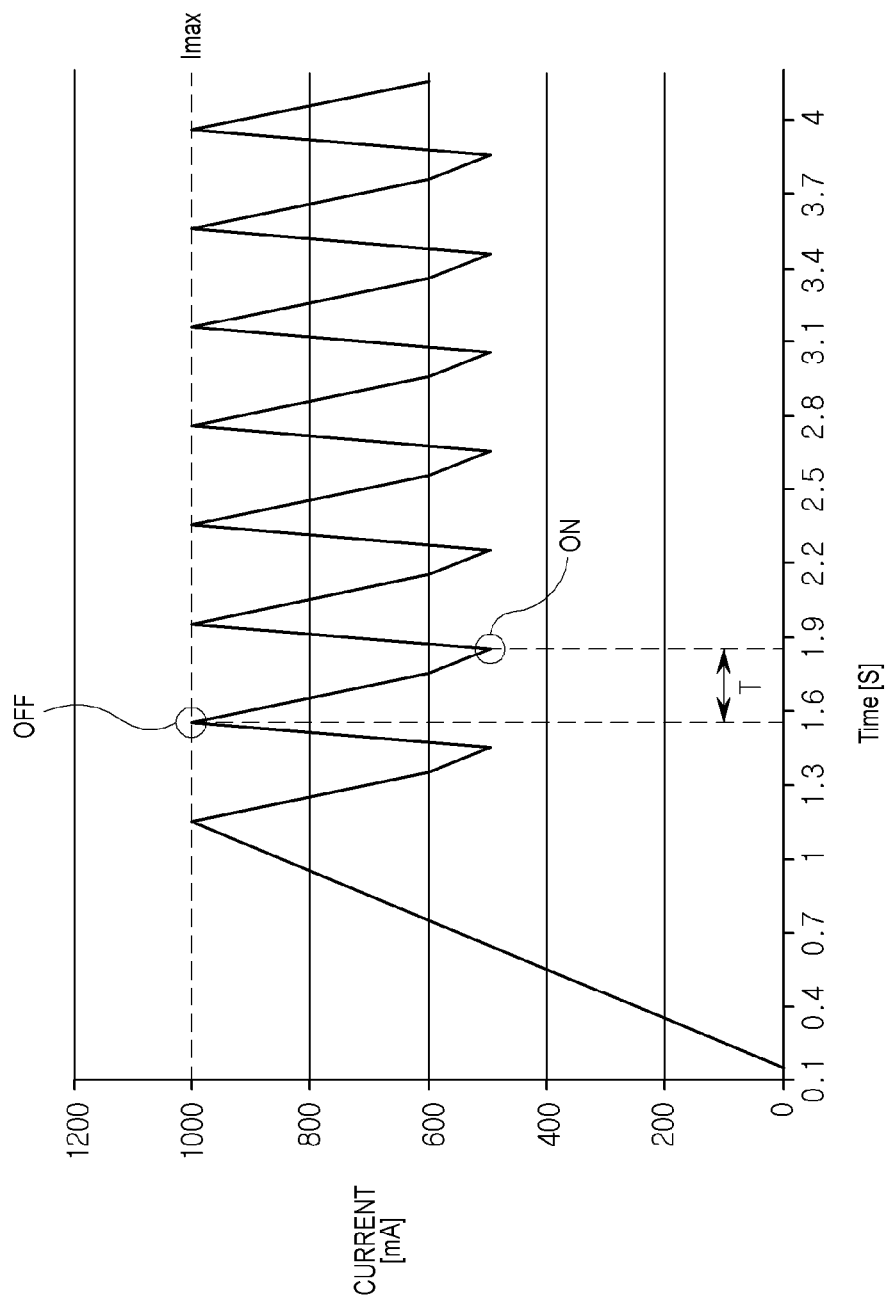
FIGS. 4 and 5 are diagrams for explaining a control module of FIG. 2.

First, referring to FIG. 4, a case where only a maximum set current (Imax) is set as the set current will be described as an example.

The control module 140 stops the amplification module 110 when the skin current reaches the maximum set current (Imax) (that is, OFF time point). When the skin current reaches the maximum set current (Imax), the control module 140 determines that the skin temperature reaches a skin temperature at which the user may be burned or feel hot to stop the amplification module 110.

The amplification module 110 stops the amplification of the direct current voltage, and applies the direct current voltage applied from the battery 14 to the conversion module 120 as it is. Accordingly, the pair of contact electrodes 12 apply to the skin an alternating current voltage having a peak-to-peak voltage lower than the voltage in a period during which the amplification module 110 operates.

The control module 140 re-drives the amplification module 110 when a set time (T) elapses after the amplification module 110 is stopped (that is, ON time point). The control module 140 counts the time from the time point at which the amplification module 110 is stopped. When the counted time reaches the set time, the control module 140 re-drives the amplification module 110. At this time, the set time is about 300 ms as an example, and may be set variously according to the setting of the skin care device 10 or the user.

Accordingly, the amplification module 110 is re-driven, and amplifies the voltage level of the direct current voltage applied from the battery 14 and applies the amplified voltage level of the direct current voltage to the conversion module 120.

Figure 5:
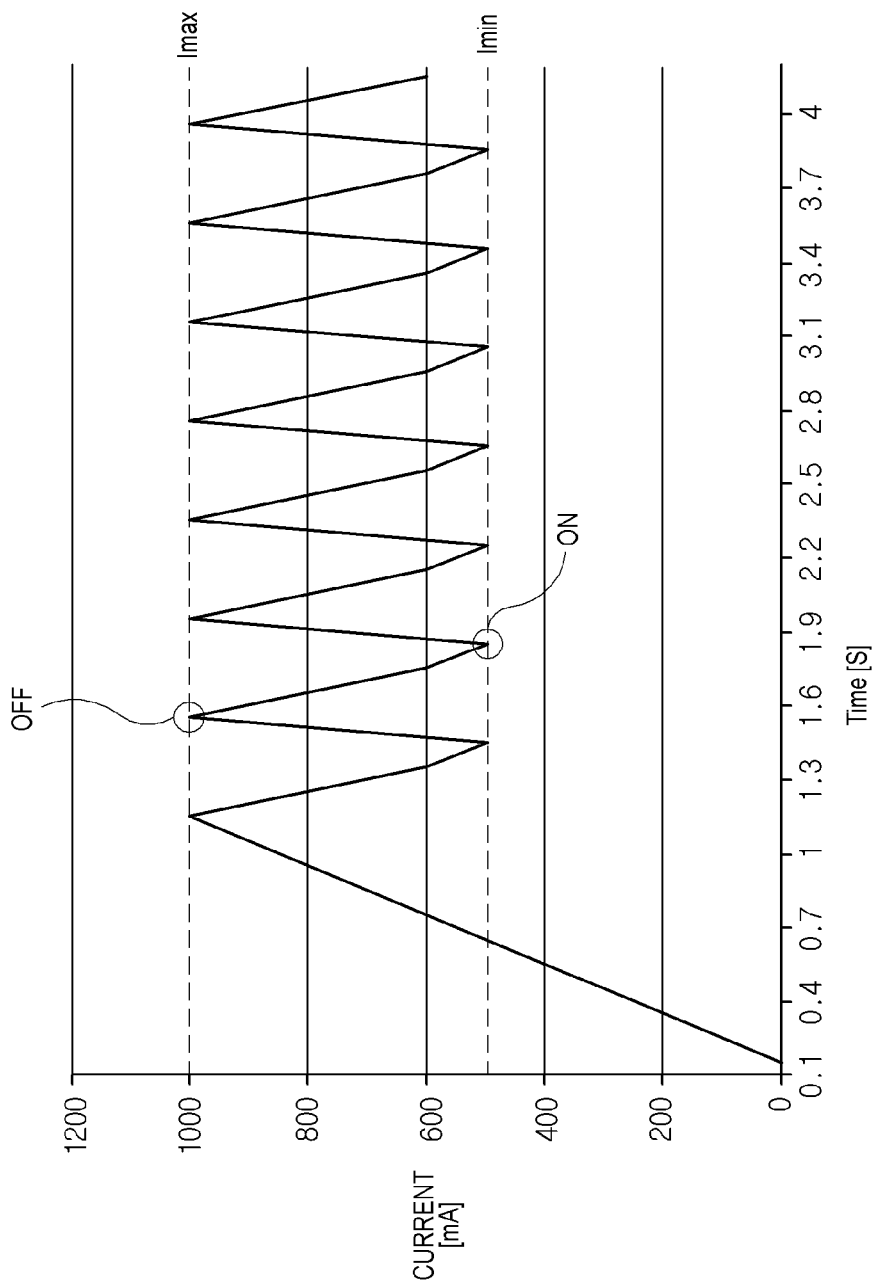

Next, a case where the maximum set current (Imax) and a minimum set current (Imin) are set as the set current will be described as an example with reference to FIG. 5.

The control module 140 stops the amplification module 110 when the skin current reaches the maximum set current (Imax) (that is, OFF time point). When the skin current reaches the maximum set current (Imax), the control module 140 determines that the skin temperature reaches a skin temperature at which the user may be burned or feel hot to stop the amplification module 110.

Accordingly, the amplification module 110 stops the amplification of the direct current voltage, and applies the direct current voltage applied from the battery 14 to the conversion module 120 as it is.

After the amplification module 110 is stopped, the control module 140 re-drives the amplification module 110 when the skin current reaches the minimum set current (Imin) (that is, ON time point). Accordingly, the amplification module 110 is re-driven, and amplifies the voltage level of the direct current voltage applied from the battery 14 and applies the amplified voltage level of the direct current voltage to the conversion module 120.

Accordingly, the apparatus for controlling the output 100 applies to the conversion module 120 the direct current voltage (that is, direct current voltage of the battery 14) having the voltage level lower than the direct current voltage boosted by the amplification module 110 during the stop period of the amplification module 110. When the skin temperature increases, the skin care device 10 to which the apparatus for controlling the output 100 is applied applies to the skin the alternating current voltage having a peak-to-peak voltage lower than usual.

Accordingly, the skin care device 10 to which the apparatus for controlling the output 100 according to the first exemplary embodiment of the present disclosure is applied may prevent an additional increase in the skin temperature, and prevent the occurrence of burns due to the increase in the skin temperature.

Further, the apparatus for controlling the output 100 according to the first exemplary embodiment of the present disclosure may minimize the change in the skin temperature as compared to the conventional skin care device 10 having a manner of turning on or off the power, thereby preventing skin care efficacy from being degraded.

The skin care device 10 has a manner of applying the current after contacting the pair of contact electrodes 12 with the skin, and there occurs a case where one of the pair of contact electrodes 12 during use is separated from the skin.

In this case, there is a problem in that the user feels hotness as the temperature increases due to the concentration of pressure on the contact electrode 12 in contact with the skin.

Further, there is a problem in that sparks are generated between the separated contact electrode 12 and the skin or the contact electrode 12 in contact with the skin, such that the user may feel sting, or get an electric shock in severe cases.

Meanwhile, when one of the contact electrodes 12 is separated from the skin, the skin resistance increases suddenly, and the skin current decreases suddenly.

The apparatus for controlling the output 100 according to the first exemplary embodiment of the present disclosure detects an event in which the contact electrode 12 is separated from the skin (hereinafter, separation event) using the aforementioned characteristics. The apparatus for controlling the output 100 solves the aforementioned problems by blocking a current path between the contact electrode 12 and the skin when the separation event is detected.

Figure 6:
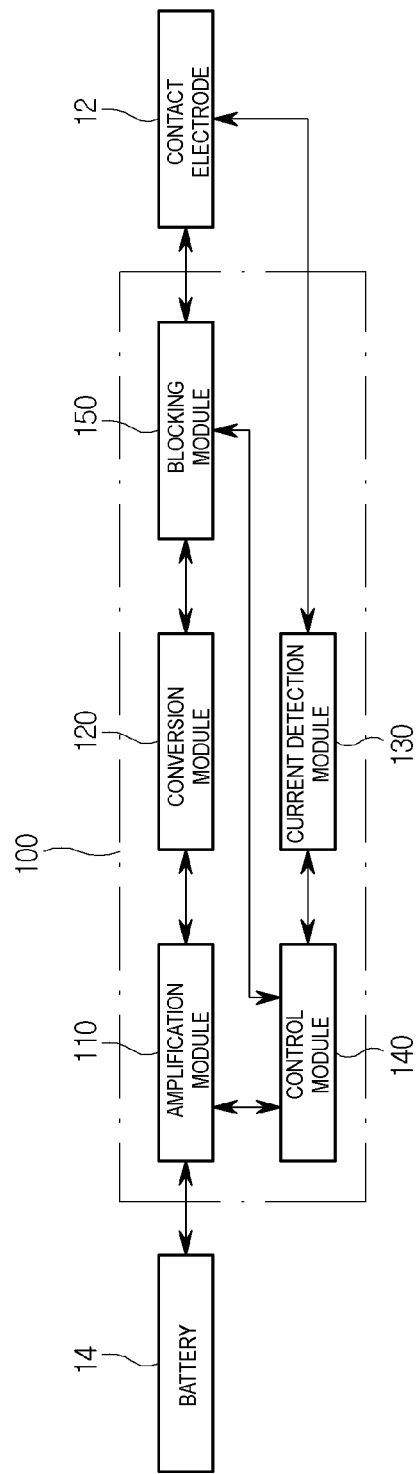
FIG. 6 is a block diagram for explaining a modified example of the apparatus for controlling the output according to the first exemplary embodiment of the present disclosure.

To this end, referring to FIG. 6, the apparatus for controlling the output 100 according to the first exemplary embodiment of the present disclosure may further include a blocking module 150.

The control module 140 generates an output blocking control signal when the skin current detected by the current detection module 130 suddenly decreases. The control module 140 generates the output blocking control signal by determining that the separation event occurs when the skin current decreases to a blocking set current or more in a state where the amplification module 110 is driven. Here, the blocking set current is a current obtained by subtracting a constant current value from the current skin current as an example, and the subtracted current value may vary depending upon the setting.

The blocking module 150 is connected between the pair of contact electrodes 12. As an example, the blocking module 150 is composed of a solid switch (or solid-state) and a resistor. The solid switch may be composed of a non-insulation type FET element, or composed of an insulation type photo coupler. The resistor is connected between the pair of contact electrodes 12. The resistor normally remains open, and is shorted to form a current path when the solid switch operates (On).

When the blocking module 150 receives the blocking control signal from the control module 140, the solid switch operates (On) to short the resistor, thereby forming the current path with the resistor. Accordingly, the blocking module 150 blocks the current path between the contact electrode 12 and the skin.

The blocking module 150 reconnects the current path between the contact electrode 12 and the skin when the set time elapses. That is, the blocking module 150 opens the resistor by stopping (OFF) the solid switch when the set time elapses after the solid switch operates. Accordingly, the blocking module 150 reconnects the current path between the contact electrode 12 and the skin.

Figure 7:
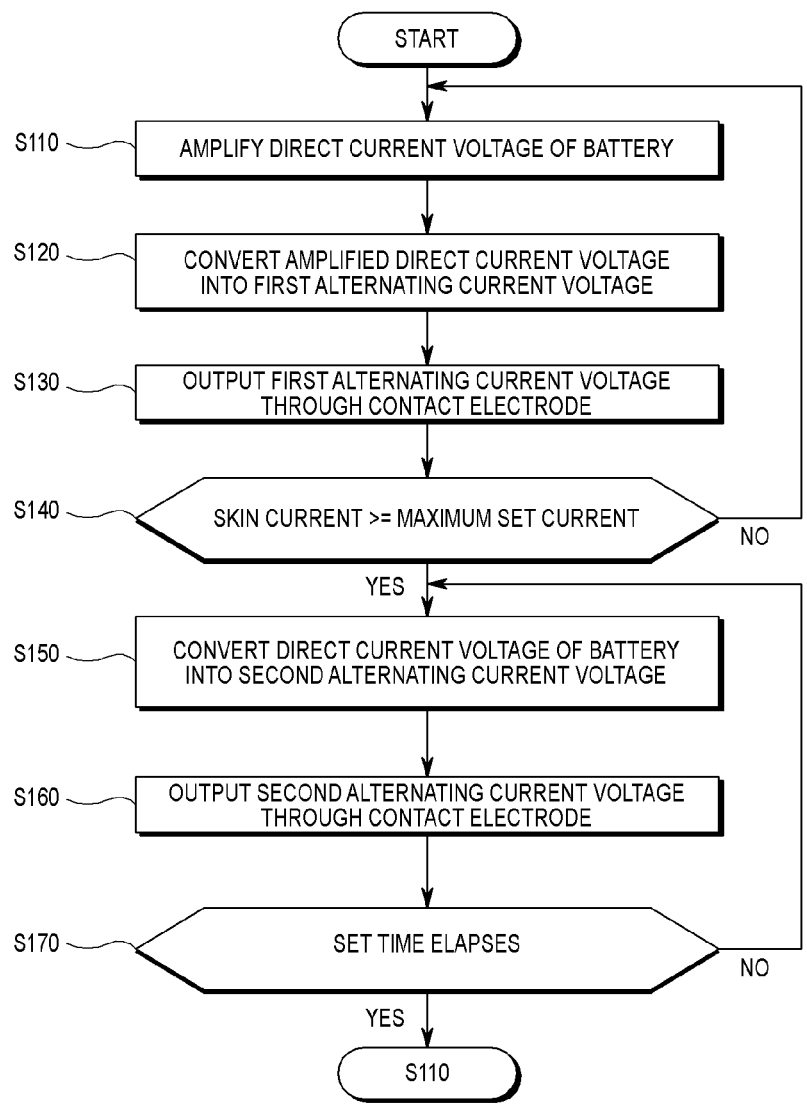
FIGS. 7 and 8 are flowcharts for explaining a method for controlling the output of the skin care device according to the first exemplary embodiment of the present disclosure.

A method for controlling the output of the skin care device 10 according to the first exemplary embodiment of the present disclosure will be described with reference to FIG. 7 as follows.

The apparatus for controlling the output 100 amplifies the direct current voltage applied from the battery 14 (S110). The apparatus for controlling the output 100 amplifies the voltage level of the direct current voltage output from the battery 14 step by step according to the output stages (for example, first stage to third stage) which is set in the skin care device 10. The apparatus for controlling the output 100 amplifies the direct current voltage to have a higher voltage level as the setting number of output stages is higher. Hereinafter, the amplified direct current voltage is referred to as an amplified direct current voltage.

As an example, when a direct current voltage of about 4.2V is applied from the battery 14, the apparatus for controlling the output 100 outputs an amplified direct current voltage of about 4.4V when the output stage is the first stage, outputs an amplified direct current voltage of about 5.1 V when the output stage is the second stage, and outputs an amplified direct current voltage of about 5.5 V when the output stage is the third stage.

The apparatus for controlling the output 100 converts the amplified direct current voltage into a first alternating current voltage (S120). The apparatus for controlling the output 100 converts the amplified direct current voltage amplified in the S110 into the first alternating current voltage having a set frequency.

The apparatus for controlling the output 100 outputs the first alternating current voltage to the skin through the contact electrode 12 of the skin care device 10 (S130). The apparatus for controlling the output 100 outputs a first alternating current voltage having a peak-to-peak voltage of about 55 V when the output stage is the first stage, outputs a first alternating current voltage having a peak-to-peak voltage of about 66 V when the output stage is the second stage, and outputs a first alternating current voltage having a peak-to-peak voltage of about 75 V when the output stage is the third stage.

Accordingly, an alternating current flows between the contact electrode 12 and the skin, and the skin resistance varies.

The apparatus for controlling the output 100 detects a skin current according to a change in skin resistance after applying the first alternating current voltage. The apparatus for controlling the output 100 detects a current value in the pair of contact electrodes 12 as the skin current. The skin current is a current value corresponding to the skin resistance. As the first alternating current voltage is applied to the skin, a change in the temperature occurs in the dermal layer of the skin, and the skin resistance varies depending upon the change in the temperature. Accordingly, the skin current increases as the skin temperature is higher, and decreases as the skin temperature decreases.

When the skin current is smaller than the maximum set current (S140; No), the apparatus for controlling the output 100 converts the amplified direct current voltage into the first alternating current voltage through the S110 to the S130 to apply the first alternating current voltage to the skin.

Meanwhile, when the skin current is the maximum set current or more (S140; Yes), the apparatus for controlling the output 100 converts the direct current voltage of the battery 14 into a second alternating current voltage (S150). When the skin current reaches the maximum set current (Imax), the apparatus for controlling the output 100 does not amplify the direct current voltage of the battery 14, and converts the direct current voltage output from the battery 14 into the second alternating current voltage.

The apparatus for controlling the output 100 outputs the second alternating current voltage to the skin through the contact electrode 12 of the skin care device 10 (S160). At this time, the second alternating current voltage output in the S160 is a voltage obtained by converting the direct current voltage of the battery 14 as it is, and the first alternating current voltage output in the S130 is a voltage obtained by converting the amplified direct current voltage amplified in the S110. Accordingly, the second alternating current voltage output to the skin in the S160 has a peak-to-peak voltage lower than the first alternating current voltage output in the S130.

The apparatus for controlling the output 100 counts the time from the time point at which the S160 is performed. When the set time (T) elapses (S170; Yes), the apparatus for controlling the output 100 repeatedly performs the aforementioned S110 to S160. As an example, the apparatus for controlling the output 100 performs the S110 to the S130 after about 300 ms elapses after the S160 to amplify the voltage level of the direct current power output from the battery 14 and then to convert the voltage level of the direct current voltage into the alternating current voltage to apply the alternating current voltage to the skin.

Figure 8:
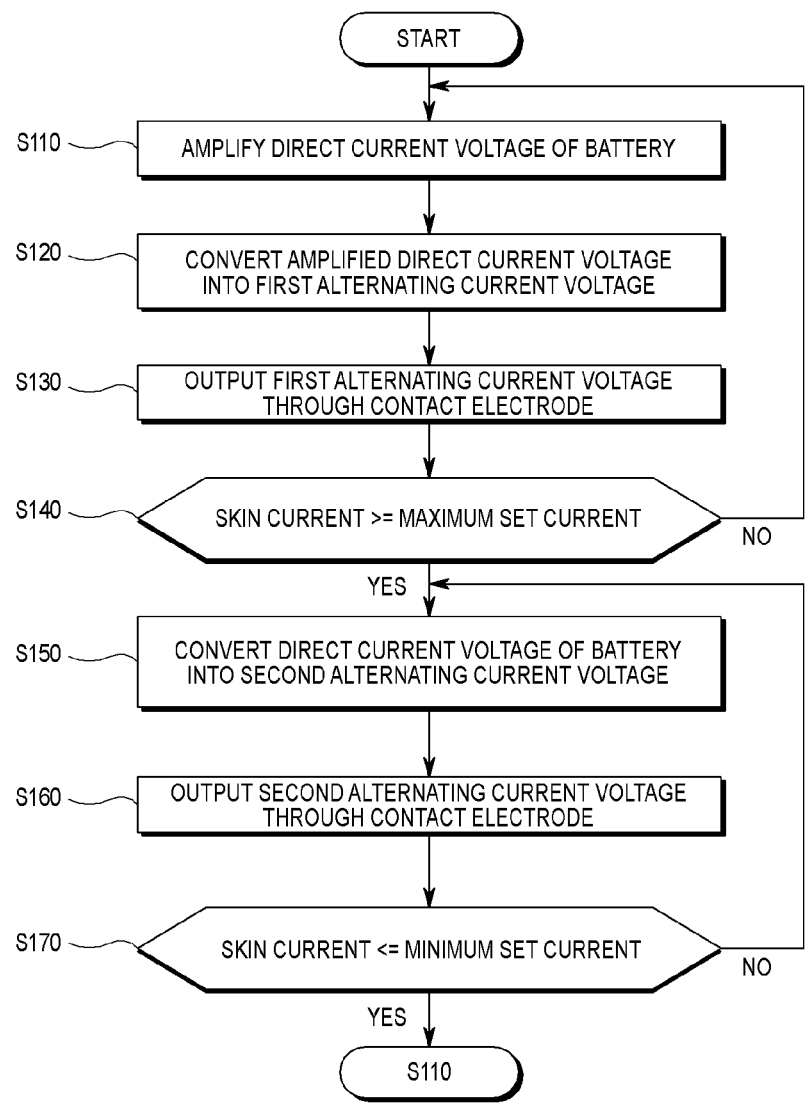

Meanwhile, referring to FIG. 8, when the skin current is the minimum set current or less (S170; Yes), the apparatus for controlling the output 100 may repeatedly perform the aforementioned S110 to S160. That is, when the skin current measured after the S160 reaches the minimum set current, the apparatus for controlling the output 100 performs the S110 to S130 to amplify the voltage level of the direct current power output from the battery 14 and then to convert the voltage level of the direct current voltage into the first alternating current voltage to apply the first alternating current voltage to the skin.

Figure 9:
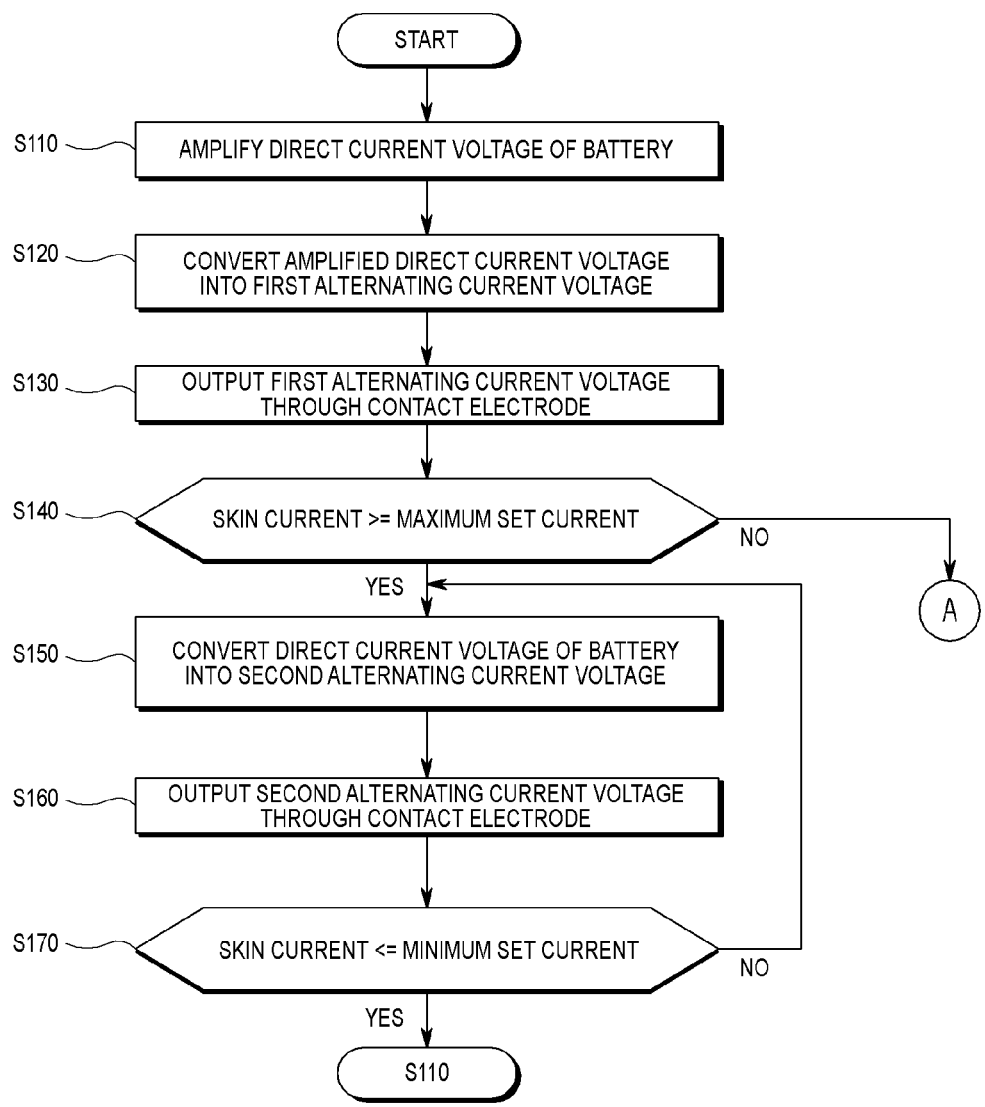
FIGS. 9 and 10 are flowcharts for explaining a modified example of the method for controlling the output of the skin care device according to the first exemplary embodiment of the present disclosure.
Figure 10:
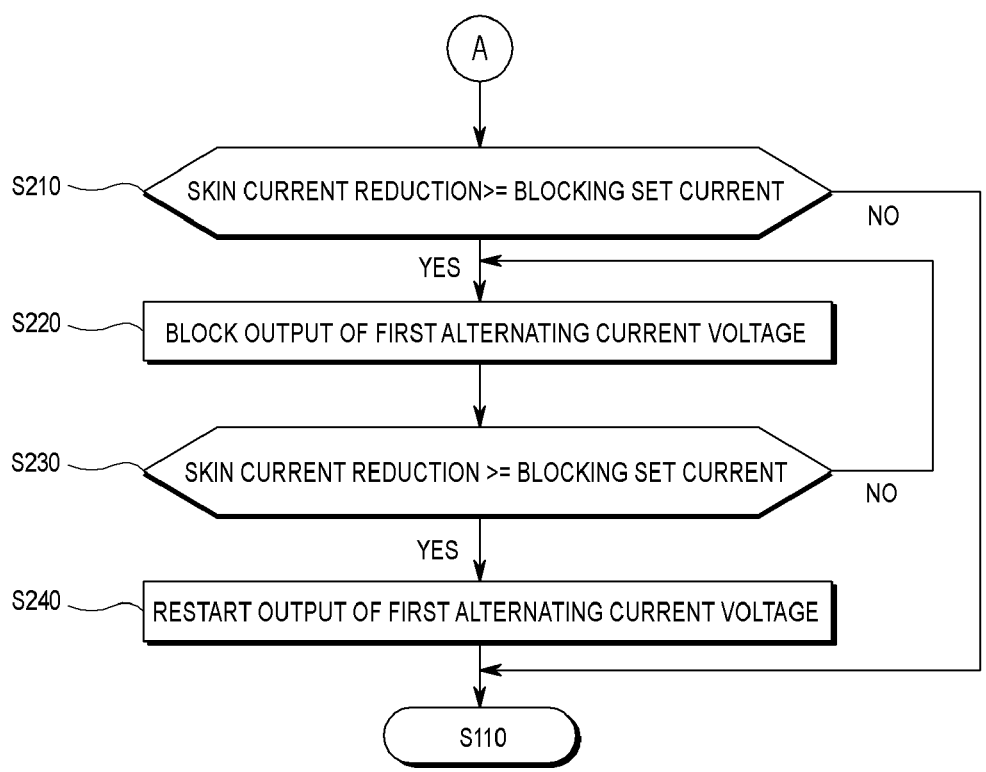

Referring to FIGS. 9 and 10, the apparatus for controlling the output 100 measures a decrease in the skin current according to the output of the first alternating current voltage through the contact electrode 12 in the S130. When the reduction in the skin current is the blocking set current or more (S210; Yes), the apparatus for controlling the output 100 blocks the output of the first alternating current voltage through the contact electrode 12 (S220). When the decrease in the skin current is the blocking set current or more, the apparatus for controlling the output 100 determines that the contact electrode 12 is separated from the skin. The apparatus for controlling the output 100 shorts the resistor connected between the pair of contact electrodes 12 to block the current path between the contact electrode 12 and the skin. That is, the apparatus for controlling the output 100 shorts the resistor to change the current path between the contact electrode 12 and the skin to the resistor. Accordingly, the apparatus for controlling the output 100 blocks the output of the first alternating current voltage to the skin.

When the set time elapses after the output of the first alternating current voltage is blocked (S230; Yes), the apparatus for controlling the output 100 resumes the output of the first alternating current voltage through the contact electrode 12 (S240). The apparatus for controlling the output 100 reconnects the current path between the contact electrode 12 and the skin when the set time elapses after blocking the output of the first alternating current voltage. That is, the apparatus for controlling the output 100 opens the resistor to reconnect the current path between the contact electrode 12 and the skin when the set time elapses. Accordingly, the skin care device 10 applies a first alternating current to the skin.

Figure 11:
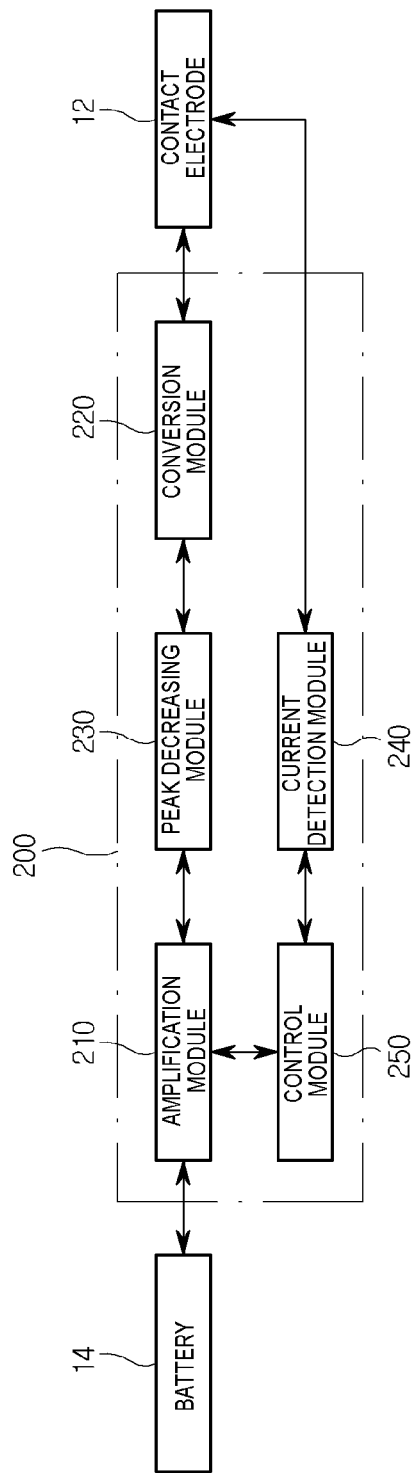
FIG. 11 is a block diagram for explaining an apparatus for controlling the output according to a second exemplary embodiment of the present disclosure.

Referring to FIG. 11, an apparatus for controlling an output 200 according to a second exemplary embodiment of the present disclosure includes an amplification module 210, a conversion module 220, a peak decreasing module 230, a current detection module 240, and a control module 250. Here, the apparatus for controlling the output 200 has been described as including all of the amplification module 210, the conversion module 220, the current detection module 240, and the control module 250, but is not limited thereto and the amplification module 210 and the conversion module 220 may also be included in the skin care device 10.

The amplification module 210 amplifies a direct current voltage output from the battery 14 under the control of the control module 250. Here, the direct current voltage amplified by the amplification module 210 means a first direct current voltage described in the claims.

The amplification module 210 amplifies the voltage level of the direct current voltage step by step according to the output stages (for example, first stage to third stage) which is set in the skin care device 10. The amplification module 210 amplifies the direct current voltage to have a higher voltage level as the output stage is higher. Hereinafter, the direct current voltage amplified by the amplification module 210 is described as an amplified direct current voltage. As an example, the amplification module 210 is a boost converter.

For example, when a direct current voltage of about 4.2 V is applied from the battery 14, the amplification module 210 outputs an amplified direct current voltage of about 4.4 V when the output stage is the first stage, outputs an amplified direct current voltage of about 5.1 V when the output stage is the second stage, and outputs an amplified direct current voltage of about 5.5 V when the output stage is the third stage.

The conversion module 220 converts the amplified direct current voltage into an alternating current voltage. The conversion module 220 converts the amplified direct current voltage amplified by the amplification module 210 into the alternating current voltage having a set frequency. At this time, as an example, the conversion module 220 is a push pull converter. Here, a first alternating current voltage described in the claims means an alternating current voltage obtained by converting the direct current voltage amplified by the amplification module 210, and a second alternating current voltage means an alternating current voltage obtained by converting the direct current voltage not amplified by the amplification module 210.

The conversion module 220 outputs the converted alternating current voltage to the pair of contact electrodes 12. The pair of contact electrodes 12 apply the alternating current voltage to the contacted skin. Accordingly, an alternating current flows between the contact electrode 12 and the skin, and the skin resistance varies.

As an example, referring to FIG. 3, the conversion module 220 outputs an alternating current voltage having a peak-to-peak voltage of about 55 V when the output stage is the first stage, outputs an alternating current voltage having a peak-to-peak voltage of about 66 V when the output stage is the second stage, and outputs an alternating current voltage having a peak-to-peak voltage of about 75 V when the output stage is the third stage.

The peak decreasing module 230 is disposed between the amplification module 210 and the conversion module 220. The peak decreasing module 230 suppresses a sudden change in the alternating current due to the alternating current voltage output from the conversion module 220. The peak decreasing module 230 reduces a high peak current (hereinafter, maximum peak current) instantaneously generated upon switching of the alternating current. To this end, as an example, the peak decreasing module 230 is composed of an inductor.

The peak decreasing module 230 reduces the maximum peak current of the alternating current to generate a phase difference between the alternating current and the alternating current voltage. The peak decreasing module 230 generates the phase difference between the alternating current and the alternating current voltage to reduce a peak value (that, peak power) of the alternating current power applied to the pair of contact electrodes 12.

Figure 12:
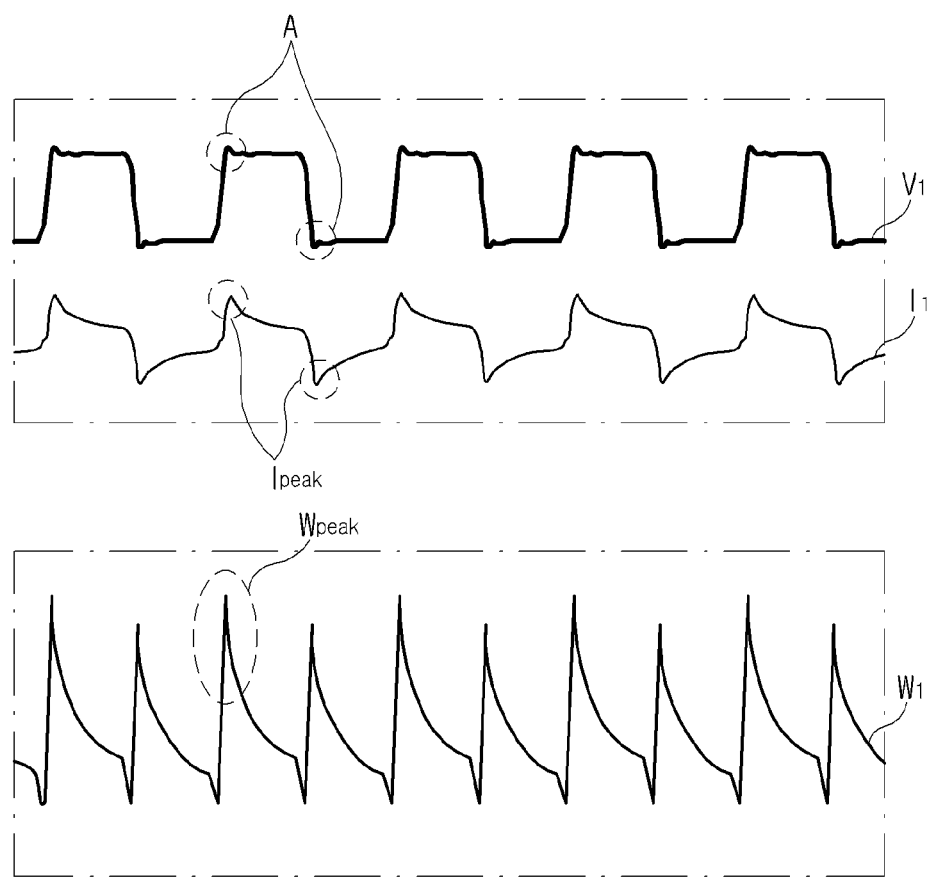
FIGS. 12 and 13 are diagrams for explaining a peak decreasing module of FIG. 11.

As an example, referring to FIG. 12, when the apparatus for controlling the output 200 does not include the peak decreasing module 230, the skin care device 10 outputs an alternating current voltage ($V_1$) having a square waveform to the skin. Accordingly, an alternating current ($I_1$) flows between the skin care device 10 and the skin, and an alternating current power ($W_1$) is applied to the skin.

At this time, a high peak current ($I_{peak}$; hereinafter, maximum peak current ($I_{peak}$)) flows instantaneously upon switching (A) of the alternating current voltage ($V_1$) output from the skin care device 10. Accordingly, a high power ($W_{peak}$; hereinafter, maximum peak power ($W_{peak}$)) is instantaneously applied to the skin.

Accordingly, the user may feel hotness or sting, or also get an electric shock in severe cases when the maximum peak power ($W_{peak}$) is instantaneously applied to the skin;

Further, since the maximum peak power ($W_{peak}$) is instantaneously output, the difference between the peak-to-peak values of the alternating current power is large, such that the skin care device 10 may not transfer the power evenly.

Figure 13:
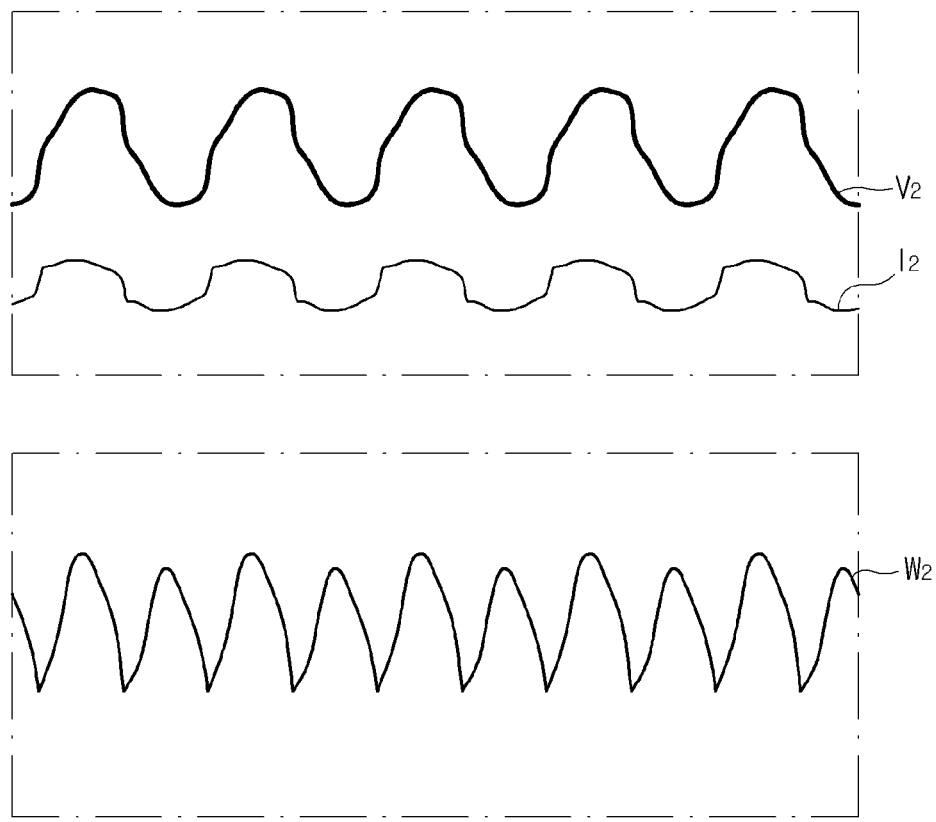

Meanwhile, referring to FIG. 13, when the apparatus for controlling the output 200 includes the peak decreasing module 230, the skin care device 10 outputs an alternating current voltage ($V_2$) having a waveform close to a sinusoidal waveform to the skin. Accordingly, an alternating current ($I_2$) flows between the skin care device 10 and the skin and an alternating current power ($W_2$) is applied to the skin.

At this time, a minute phase difference between the alternating current voltage ($V_2$) and the alternating current ($I_2$) may be generated, thereby preventing the maximum peak power from being applied to the skin instantaneously upon switching of the alternating current voltage ($V_2$) output from the skin care device 10.

Accordingly, the apparatus for controlling the output 200 may prevent the user's hotness, sting, and electric shock due to the maximum peak power.

Further, the apparatus for controlling the output 200 decreases the peak power applied from the skin care device 10 to the skin to enable even power transmission.

The current detection module 240 detects a skin current according to a change in the skin resistance after the alternating current voltage is applied. The current detection module 240 detects a current value in the pair of contact electrodes 12 as the skin current. The detecting module transmits the detected skin current to the control module 250.

The skin current detected by the current detection module 240 is a current value corresponding to the skin resistance. At this time, as the alternating current voltage is applied to the skin, a change in the temperature occurs in the dermal layer of the skin, and the skin resistance varies depending upon the change in the temperature. Accordingly, the skin current detected by the current detection module 240 increases as the skin temperature is higher, and decreases as the skin temperature decreases.

The control module 250 controls the driving of the amplification module 210 based on the skin current detected by the current detection module 240. The control module 250 controls the driving of the amplification module 210 based on the skin current detected by the current detection module 240 and a set current.

First, a case where only the maximum set current (Imax) is set as the set current will be described as an example (see FIG. 4 in the first exemplary embodiment).

The control module 250 stops the amplification module 210 when the skin current reaches the maximum set current (Imax) (that is, OFF time point). When the skin current reaches the maximum set current (Imax), the control module 250 determines that the skin temperature reaches a skin temperature at which the user may be burned or feel hot to stop the amplification module 210.

The amplification module 210 stops the amplification of the direct current voltage, and applies the direct current voltage applied from the battery 14 to the conversion module 220 as it is. Accordingly, the pair of contact electrodes 12 apply to the skin an alternating current voltage having a peak-to-peak voltage lower than the voltage in a period during which the amplification module 210 operates.

The control module 250 re-drives the amplification module 210 when the set time (T) elapses after the amplification module 210 is stopped (that is, ON time point). The control module 250 counts the time from the time point at which the amplification module 210 is stopped. When the counted time reaches the set time, the control module 250 re-drives the amplification module 210. At this time, the set time is about 300 ms as an example, and may be set variously according to the setting of the skin care device 10 or the user.

Accordingly, the amplification module 210 is re-driven, and amplifies the voltage level of the direct current voltage applied from the battery 14 and then applies the amplified voltage level of the direct current voltage to the conversion module 220.

Next, a case where the maximum set current (Imax) and a minimum set current (Imin) are set as the set current will be described as an example (see FIG. 5 in the first exemplary embodiment).

The control module 250 stops the amplification module 210 when the skin current reaches the maximum set current (Imax) (that is, OFF time point). When the skin current reaches the maximum set current (Imax), the control module 250 determines that the skin temperature reaches a skin temperature at which the user may be burned or feel hot to stop the amplification module 210.

Accordingly, the amplification module 210 stops the amplification of the direct current voltage, and applies the direct current voltage applied from the battery 14 to the conversion module 220 as it is.

The control module 250 re-drives the amplification module 210 when the skin current reaches the minimum set current (Imin) after the amplification module 210 is stopped (that is, ON time point). Accordingly, the amplification module 210 is re-driven, and amplifies the voltage level of the direct current voltage applied from the battery 14 and then applies the amplified voltage level of the direct current voltage to the conversion module 220.

Accordingly, the apparatus for controlling the output 200 applies to the conversion module 220 a direct current voltage (that is, direct current voltage of the battery 14) having a voltage level lower than the direct current voltage boosted by the amplification module 210 during the stop period of the amplification module 210. When the skin temperature increases, the skin care device 10 to which the apparatus for controlling the output 200 is applied applies to the skin an alternating current voltage having a peak-to-peak voltage lower than usual.

Accordingly, the skin care device 10 to which the apparatus for controlling the output 200 according to the second exemplary embodiment of the present disclosure is applied may prevent an additional increase in the skin temperature, and prevent the occurrence of burns due to the increase in the skin temperature.

Further, the apparatus for controlling the output 200 according to the second exemplary embodiment of the present disclosure may minimize the change in the skin temperature as compared to the conventional skin care device 10 operating in a manner of turning on or off the power, thereby preventing the skin care efficacy from being degraded.

The skin care device 10 operates in a manner of applying the current after contacting the pair of contact electrodes 12 with the skin, and there occurs a case where one of the pair of contact electrodes 12 during use is separated from the skin.

In this case, there is a problem in that the user feels hotness as the temperature increases due to the concentration of pressure on the contact electrode 12 in contact with the skin.

Further, there is a problem in that sparks are generated between the separated contact electrode 12 and the skin or the contact electrode 12 in contact with the skin, such that the user may feel sting, or get an electric shock in severe cases.

Meanwhile, when one of the contact electrodes 12 is separated from the skin, the skin resistance increases suddenly, and the skin current decreases suddenly.

The apparatus for controlling the output 200 according to the second exemplary embodiment of the present disclosure detects an event in which the contact electrode 12 is separated from the skin (hereinafter, a separation event) using the aforementioned characteristics. The apparatus for controlling the output 200 solves the aforementioned problems by blocking a current path between the contact electrode 12 and the skin when the separation event is detected.

Figure 14:
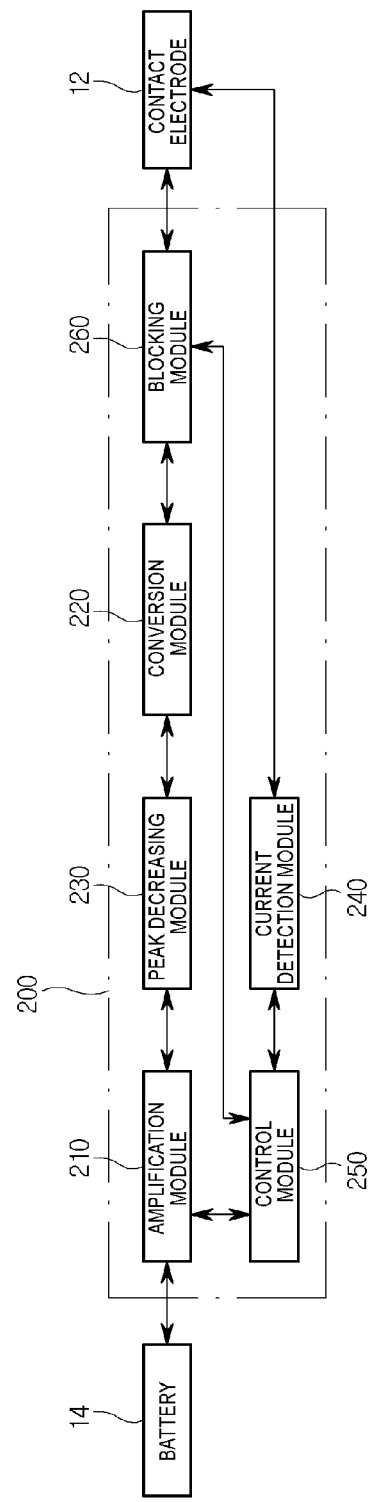
FIG. 14 is a block diagram for explaining a modified example of the apparatus for controlling the output according to a second exemplary embodiment of the present disclosure.

To this end, referring to FIG. 14, the apparatus for controlling the output 200 according to the second exemplary embodiment of the present disclosure may further include a blocking module 260.

The control module 250 generates an output blocking control signal when the skin current detected by the current detection module 240 suddenly decreases. The control module 250 determines that the separation event occurs when the skin current decreases to the blocking set current or more in a state where the amplification module 210 is driven to generate an output blocking control signal. Here, the blocking set current is a current obtained by subtracting a constant current value from the current skin current as an example, and the subtracted current value may vary depending on the setting.

The blocking module 260 is connected between the pair of contact electrodes 12. As an example, the blocking module 260 is composed of a solid switch (or solid-state) and a resistor. The solid switch may be composed of a non-insulation type PET element or composed of an insulation type photo coupler. The resistor is connected between the pair of contact electrodes 12. The resistor normally remains open, and is shorted to form the current path when the solid switch operates (On).

When the blocking module 260 receives the blocking control signal from the control module 250, the solid switch operates (On) to short the resistor, thereby forming the current path with the resistor. Accordingly, the blocking module 260 blocks the current path between the contact electrode 12 and the skin.

The blocking module 260 reconnects the current path between the contact electrode 12 and the skin when the set time elapses. That is, the blocking module 260 stops (OFF) the solid switch to open the resistor when the set time elapses after the solid switch operates. Accordingly, the blocking module 260 reconnects the current path between the contact electrode 12 and the skin.

As described above, although the preferred exemplary embodiment according to the present disclosure has been described, it is understood that changes may be made in various forms, and those skilled in the art may practice various changed examples and modified examples without departing from the claims of the present disclosure.

The invention claimed is:

1. An apparatus for controlling an output of a skin care device configured to apply an alternating current voltage to a skin through a pair of contact electrodes, the apparatus for controlling the output comprising:
   an amplification module configured to amplify and output a direct current voltage;
   a conversion module configured to convert the direct current voltage output from the amplification module into an alternating current voltage having a set frequency to output the alternating current voltage to the pair of contact electrodes;
   a peak decreasing module configured to decrease a maximum peak current of an alternating current generated upon switching of the alternating current voltage output from the conversion module by generating a phase difference between the alternating current and the alternating current voltage output from the conversion module;
   a current sensor configured to detect a skin current according to a change in a resistance of the skin to which the alternating current voltage is applied;
   a controller configured to control the driving of the amplification module based on the skin current; and
   a blocking module configured to be connected between the pair of contact electrodes, and configured to form a current path between the pair of contact electrodes to block a current path between the contact electrodes and the skin when the skin current decreases to a blocking set current or more,
   wherein the peak decreasing module decreases a peak power of the alternating current power applied to the skin through the pair of contact electrodes,
   wherein the controller stops the amplification module when the skin current is a maximum set current or more, and re-drives the amplification module when the skin current is a minimum set current or less after stopping the amplification module,
   the conversion module outputs a first alternating current voltage when the amplification module is driven, and outputs a second alternating current voltage having a peak-to-peak voltage lower than the first alternating current voltage when the amplification module is stopped,
   wherein the blocking module applies the alternating current power to the pair of contact electrodes when a set time elapses after blocking a current path,
   wherein the conversion module outputs the first alternating current voltage and the second alternating current voltage, and
   wherein the first alternating current voltage and the second alternating current voltage have the set frequency, and the second alternating current voltage has a voltage level lower than the first alternating current voltage.

2. The apparatus for controlling the output of claim 1, wherein the amplification module outputs a first direct current voltage obtained by amplifying the direct current voltage upon driving, and outputs a second direct current voltage which is a voltage level lower than the first direct current voltage upon stopping.

3. A method for controlling an output of a skin care device configured to apply an alternating current voltage to a skin through a pair of contact electrodes, the method comprising:
   amplifying a direct current voltage;
   converting the amplified direct current voltage into a first alternating current voltage having a set frequency;
   outputting the first alternating current voltage through the pair of contact electrodes;
   detecting a skin current according to a change in a resistance of the skin to which the first alternating current voltage is applied;
   stopping the amplifying when the skin current is a maximum set current or more;
   converting the direct current voltage into a second alternating current voltage having a set frequency when the amplifying is stopped;
   outputting the second alternating current voltage having a peak-to-peak voltage lower than the first alternating current voltage through the pair of contact electrodes;
   decreasing a maximum peak current of an alternating current generated upon switching of the first and second alternating current voltage output from a conversion module by generating a phase difference between the alternating current and the alternating current voltage;
   blocking a current path between the contact electrodes and the skin by forming a current path between the pair of contact electrodes when the skin current decreases to a blocking set current or more;
   restarting the output of the first alternating current voltage by restarting amplifying when the skin current is a minimum set current or less after the outputting of the second alternating current voltage, and
   re-applying the first alternating current voltage to the pair of contact electrodes when a set time elapses after the blocking of the first alternating current voltage;
   wherein the decreasing a maximum peak current decreases a peak power of the alternating current power applied to the skin through the pair of contact electrodes, and
   wherein the first alternating current voltage and the second alternating current voltage have the set frequency, and the second alternating current voltage has a voltage level lower than the first alternating current voltage.

* * * * *